United States Patent [19]
Montgomery

[11] Patent Number: 5,603,924
[45] Date of Patent: Feb. 18, 1997

[54] NON-YELLOWING ARTIFICIAL FINGERNAIL COMPOSITION

[75] Inventor: Robert E. Montgomery, Los Angeles, Calif.

[73] Assignee: OPI Products, Inc.

[21] Appl. No.: 511,282

[22] Filed: Aug. 4, 1995

Related U.S. Application Data

[63] Continuation of Ser. No. 841,429, Feb. 26, 1992.

[51] Int. Cl.$^6$ ..................................................... A61K 7/043
[52] U.S. Cl. ...................... 424/61; 424/78.02; 424/78.03; 424/401; 524/376; 524/388; 525/303
[58] Field of Search .................... 424/401, 61, 78.02, 424/78.03; 524/376, 388; 525/303

[56] References Cited

U.S. PATENT DOCUMENTS

| | | | |
|---|---|---|---|
| 3,905,376 | 9/1975 | Johnson et al. | 128/595 |
| 4,229,431 | 10/1980 | Lee et al. | 424/61 |
| 4,871,534 | 10/1989 | Montgomery | 424/61 |
| 5,110,584 | 5/1992 | Medri et al. | 424/61 |

*Primary Examiner*—Neil S. Levy
*Attorney, Agent, or Firm*—Blakely Sokoloff Taylor & Zafman

[57] ABSTRACT

This present invention is a composition for making artificial fingernails which is non-yellowing, and which polymerizes rapidly during use, and a method of making such composition, as well as a method of using the composition in the formation of artificial fingernails. Compositions of this invention comprise a liquid binder portion containing one or more monomeric methacrylate esters; optionally one or more di-, tri-, or multi-functional methacrylate esters, an alcohol, and a tertiary amine accelerator; a polymeric filler portion containing a finely divided polymer, and an organic peroxide polymerization initiator. The compositions of the present invention will polymerize in from about 120 seconds to about 360 seconds, resulting in a hard and resilient non-yellowing polymer.

7 Claims, No Drawings

NON-YELLOWING ARTIFICIAL FINGERNAIL COMPOSITION

This is a continuation of application Ser. No. 07/841,429, filed Feb. 26, 1992 now pending.

BACKGROUND OF THE INVENTION

1. Field of the Invention

This invention relates to compositions that are useful for forming artificial fingernails and protective coatings on human fingernails. In particular, the present invention comprises self-curing compositions which polymerize rapidly at ambient temperatures and are resistant to yellowing, when applied over human fingernails to protect, adorn, extend, and/or decorate them.

2. Prior Art

The prior art discloses a variety of useful, self-curing compositions that can be applied to human fingernails for the purpose of forming an artificial fingernail. In general, these compositions are two-part systems which consist of a liquid portion (herein referred to as a binder) and a powder portion (herein referred to as a polymeric filler). In particular, such compositions are described in U.S. Pat. Nos. 4,104,333, 4,229,431, 4,260,701, 4,626,428, 4,669,491, 4,708,866, 4,718,957, and 4,871,534.

The liquid binders as described therein comprise the following ingredients:

(a) a monomeric acrylate or methacrylate ester such as ethyl methacrylate, tetrahydrofurfuryl methacrylate, methoxyethyl methacrylate, methoxyethoxyethyl methacrylate, and others, (b) a di-, tri-, or multi-functional acrylate or methacrylate ester such as ethylene glycol dimethacrylate, diethylene glycol dimethacrylate, 1,4-butanediol dimethacrylate, trimethylolpropane trimethacrylate, and others, and (c) a tertiary amine accelerator such as N,N-dimethyl-p-toluidine.

Optionally, the liquid binders may contain polymerization inhibitors (such as methyl ether of hydroquinone or BHT), dyes, and ultraviolet light stabilizers.

The polymeric filler portion of the prior art compositions generally comprise the following ingredients:

(a) a finely divided polymeric methacrylate, such as poly(ethyl methacrylate) or copolymeric methacrylate, such as a 70:30 molar ratio comprising poly(ethyl-co-methyl methacrylate), and (b) an organic peroxide polymerization initiator such as benzoyl peroxide.

Optionally, the polymeric filler portions may contain pigments (such as titanium dioxide), secondary polymers (such as poly[vinyl acetate]) and flow modifiers (such as fumed silica).

The procedure of forming an artificial fingernail in situ (i.e., on a human fingernail) is an exacting art which is performed by trained and licensed personnel. An artist's-type brush is first dipped in a reservoir containing the liquid binder portion in order to wet the brush fibers. The brush tip is then transferred to a reservoir containing the polymeric filler portion in such a way as to allow the wetted brush to absorb sufficient powder to form a dough-like mass at the end of the brush. This dough-like mass is then transferred to the surface of the human fingernail and subsequently shaped with the brush to form the desired coating and/or artificial fingernail extension. Forms are often attached to the end of the fingernail to provide a surface on which to apply the extension in order to extend the length of the artificial nail beyond the length of the natural nail.

In the process of mixing the liquid binder with the polymeric filler, a free-radical polymerization process is initiated by the dissolution of the organic peroxide (provided by the polymeric filler) in the liquid binder. As the organic peroxide dissolves in the liquid binder, it produces free-radicals through interaction with the tertiary amine accelerator already present in the binder. A proper balance of initiator and accelerator, in addition to liquid binder and polymeric filler, allows sufficient working time to shape the dough-like mass into the desired form, yet causes polymerization (solidification) to ensue within a reasonable length of time. It is desirable for the mass to begin the polymerization process within from about 120 seconds to about 360 seconds from the time of initial mixing of the liquid binder and the polymeric filler. The ideal and preferred polymerization time is from about 180 seconds to about 300 seconds from the time of initial mixing. If the time for polymerization is too long, there is an increased likelihood of damage to the surface of the coating before it is fully hardened, and the added inconvenience of a long waiting time for drying. If polymerization occurs too quickly, the coating may be hardened before application is completed.

The time of onset of polymerization can be controlled by varying the amounts of the organic peroxide (generally contained and dispersed within the polymeric filler portion of artificial fingernail compositions) and tertiary amine (found in the liquid binder portion). By increasing the levels of both organic peroxide and tertiary amine, a more rapid polymerization may be achieved. However, excess organic peroxides and tertiary amines are believed to cause the production of chromogenic substances which result in the discoloration of artificial fingernails (often referred to as "yellowing"). Thus, a practical limit on the highest amounts of both organic peroxides and tertiary amines is reached whereby further decrease in polymerization time is accompanied by an increase in polymer discoloration.

It would thus be advantageous to provide a rapid-polymerizing, yet non-yellowing artificial fingernail composition, which utilizes the same application methods as the prior art compositions.

It would also be advantageous to provide an artificial fingernail composition capable of polymerizing in from about 120 seconds to about 360 seconds without the yellowing associated with the heretofore required high organic peroxide and tertiary amine concentrations utilized in the prior art.

SUMMARY OF THE INVENTION

In accordance with the aforementioned description and desire to provide an improved self-curing artificial fingernail composition, the present invention includes compositions which provide non-yellowing artificial fingernails, and polymerizes rapidly during use, and a method of making such composition, as well as a method of using the composition in the formation of artificial fingernails.

Compositions of this invention comprise:

(1) A liquid binder portion containing:

(a) one or more monomeric methacrylate esters, (b) optionally and preferably, one or more di-, tri-, or multi-functional methacrylate esters, (c) an unsaturated or saturated alcohol, and (d) a tertiary amine accelerator (2) A polymeric filler portion containing:
(a) a finely divided polymer, and
(b) an organic peroxide polymerization initiator.

Upon mixing (1) and (2) above, according to procedures described above, and shaping the resultant mass into the desired shape, the compositions of the instant invention will polymerize in from about 120 seconds to about 360 seconds, resulting in a hard and resilient non-yellowing polymer.

The total combined amount of tertiary amine accelerator and organic peroxide polymerization initiator in the present invention is substantially less than that amount necessary to achieve comparable polymerization rates in prior art compositions, due to the surprising accelerating effect of the alcohol compound.

It is thus an object of the present invention to provide a rapid-polymerizing, yet non-yellowing artificial fingernail composition.

It is another object of the present invention to provide a method of making the rapid-polymerizing, yet non-yellowing artificial fingernail composition of the present invention.

It is yet another a object of the present invention to provide a method of making artificial fingernails which are rapid-polymerizing, yet non-yellowing in accordance with the present invention.

It is also an object of the present invention to provide an artificial fingernail composition capable of polymerizing in from about 120 seconds to about 360 seconds without the yellowing associated with the heretofore required high organic peroxide and tertiary amine concentrations utilized in the prior art.

DETAILED DESCRIPTION OF THE INVENTION

This invention comprises self-curing compositions that are useful for fashioning artificial fingernails and/or decorative coatings in situ on a human fingernail. In general, these compositions comprise a liquid binder and a polymeric filler, which, upon being admixed at the time of use, polymerize to a hard, fused polymer in the shape of an artificial fingernail and/or decorative coating in from about 120 seconds to about 360 seconds at ambient temperatures.

The liquid binder portion is comprised of the following ingredients, based upon the total weight of liquid binder:

(a) from about 10 percent to about 95 percent of a methacrylate monomer including, but not limited to, ethyl methacrylate, n-butyl methacrylate, isobutyl methacrylate, n-propyl methacrylate, isopropyl methacrylate, tert-butyl methacrylate, methoxyethoxyethyl methacrylate, ethoxyethoxyethyl methacrylate, benzyl methacrylate, phenethyl methacrylate, and combinations thereof;

(b) optionally and preferably, from about 1 percent to about 50 percent of a di-, tri-, or multi-functional methacrylate crosslinker including, but not limited to, ethylene glycol dimethacrylate, diethylene glycol dimethacrylate, triethylene glycol dimethacrylate, tetraethylene glycol dimethacrylate, poly(ethylene glycol) dimethacrylate, 1,3-butanediol dimethacrylate, 1,4-butanediol dimethacrylate, 1,6-hexanediol dimethacrylate, 1,12-dodecanediol dimethacrylate, neopentyl glycol dimethacrylate, trimethylolpropane trimethacrylate, and combinations thereof;

(c) from about 1 percent to about 50 percent of an unsaturated or saturated alcohol compound including, but not limited to, hydroxyethyl methacrylate, hydroxypropyl methacrylate, hydroxybutyl methacrylate, propylene glycol monomethyl ether, diethylene glycol monomethyl ether, diethylene glycol monoethyl ether, isopropyl alcohol, propylene glycol, 1,4-butylene glycol, neopentyl glycol monomethacrylate and combinations thereof, and;

(d) from about 0.1 percent to about 5.0 percent of a tertiary amine polymerization accelerator, selected from the group including, but not limited to, N,N-dimethyl-p-toluidine, N,N-dihydroxyethyl-p-toluidine, N,N-dimethyl aniline, and 4-(dimethylamino)phenethyl alcohol (U.S. Pat. No. 4,284,551).

In addition to the above components, the liquid binder may optionally contain a polymerization inhibitor such as butylated hydroxytoluene (BHT) or methyl ether of hydroquinone (MEHQ) to prevent premature reaction of the methacrylate monomers prior to use, to provide adequate long term stability, and to control the polymerization speed. Increases in polymerization inhibitors will lengthen the time observed between the initial admixture of liquid binder and polymeric filler, and the onset of polymerization. Also, ultraviolet light stabilizers such as Tinuvin P (Ciba Geigy Corp.) and Uvinul M-40 (BASF) may be included in the liquid binder portion to prevent light-activated polymerization and provide additional discoloration resistance to the resultant polymerized artificial fingernail. Finally, auxiliary components such as dyes may be included so as to modify color and final appearance of the artificial fingernail.

The polymeric filler portion is comprised of the following ingredients, based upon the dry weight of filler:

(a) from about 95 percent to about 99.9 percent of a finely divided polymer selected from the group including, but not limited to, poly(ethyl methacrylate), poly(methyl methacrylate), poly(ethyl-co-methyl methacrylate), poly(butyl methacrylate), poly(methyl-co-butyl methacrylate), poly(vinyl acetate), poly(vinyl butyral), poly(ethyl-co-butyl methacrylate), (b) from about 0.1 percent to about 5.0 percent of an organic peroxide polymerization initiator, preferably benzoyl peroxide.

The polymeric filler portion may optionally include pigments, such as titanium dioxide, secondary polymers, such as finely divided poly(vinyl acetate), and flow modifiers, such as fumed silica.

Essential to the practice of the instant invention is the inclusion in the liquid binder portion of the composition, an alcohol compound possessing one or more hydroxyl (—OH) moieties. It has been unexpectedly discovered that the presence of an hydroxyl-containing alcohol within the liquid binder portion of self-curing artificial fingernail compositions can greatly accelerate the polymerization time achievable at given concentrations of organic peroxide initiator and tertiary amine accelerator. Conversely, the compositions of this invention can provide comparable polymerization times to prior art artificial fingernail compositions, while utilizing lower overall concentrations of organic peroxide initiator and tertiary amine accelerator. Lower initiator and accelerator concentrations will provide artificial fingernails with a greatly reduced propensity towards yellowing.

EXAMPLE I

Accelerating Effect of Compounds Containing Hydroxyl Moieties

The following examples demonstrate the accelerating effect of an unsaturated alcohol, hydroxyethyl methacrylate, on a typical artificial fingernail composition.

| Liquid Binder | A | B | C |
|---|---|---|---|
| Ethyl methacrylate | 93.000% | 83.000% | 73.000% |
| Ethylene glycol dimethacrylate | 6.000 | 6.000 | 6.000 |
| Hydroxyethyl methacrylate | — | 10.000 | 20.000 |
| N,N-dimethyl-p-toluidine | 1.000 | 1.000 | 1.000 |
| Total | 100.000% | 100.000% | 100.000% |

| POLYMERIC FILLER | |
|---|---|
| Poly(ethyl-co-methyl methacrylate) (70:30 mole ratio) | 98.60% |
| Benzoyl peroxide | 1.40 |
| Total | 100.00 |

In order to determine the polymerization time of the above compositions, 2.00 grams of liquid binder was combined with 5.40 grams of polymeric filler, mixed manually for 30 seconds, a thermometer placed directly within the resultant dough-like mass, and placed in a water bath equilibrated at 25 degrees Celsius. Since acrylate and methacrylate polymerizations are exothermic in nature, an increase in temperature of the polymerizing mass was indicative of the onset of polymerization. Polymerization time was recorded when the mass showed an increase of 10 degrees Celsius; the results below are the averages of five trials.

| Example | Polymerization Time |
|---|---|
| A | 320 seconds |
| B | 260 seconds |
| C | 170 seconds |

A comparison of the polymerization times for the above examples clearly demonstrates the accelerating effect of hydroxyethyl methacrylate. The following examples show the accelerating effect of a variety of hydroxyl-containing compounds. Polymerization times were determined as above, utilizing the same polymeric filler composition.

| Liquid Binder | Amount |
|---|---|
| Ethyl methacrylate | 83.000% |
| X | 10.000 |
| Ethylene glycol dimethacrylate | 6.000 |
| N,N-dimethyl-p-toluidine | 1.000 |
| Total | 100.000 |

| Example | X | Polymerization Time |
|---|---|---|
| D | Hydroxypropyl methacrylate | 250 seconds |
| E | Isopropyl alcohol | 265 seconds |
| F | Propylene glycol monomethyl ether | 260 seconds |
| G | Methoxyethoxyethanol | 250 seconds |
| H | Propylene glycol | 220 seconds |
| I | 1,4-butylene glycol | 230 seconds |
| J | Neopentyl glycol monomethacrylate | 260 seconds |

EXAMPLE II

Effect of Organic Peroxide and Tertiary Amine Concentrations on Yellowing of Artificial Fingernail Compositions In order to demonstrate the relationship between initiator/accelerator concentrations and yellowing of the resultant artificial fingernail polymer, a series of compositions was prepared which compared initiator/accelerator level with polymerization time and extent of yellowing. Polymerization time was determined as above, and yellowing was determined visually, (after exposure to ultraviolet light from a UVA lamp @2 mW per square centimeter, for hours) based on a scale of 1 to 10, 10 being the most yellow.

| Liquid Binder | Amount |
|---|---|
| Ethyl methacrylate | 94.00 − X |
| Ethylene glycol dimethacrylate | 6.00 |
| N,N-dimethyl-p-toluidine | X |
| Total | 100.00 |

| POLYMERIC FILLER | |
|---|---|
| Poly(ethyl-co-methyl methacrylate) (70:30 mole ratio) | 100.00 − Y |
| Benzoyl peroxide | Y |
| Total | 100.00 |

| POLYMERIZATION | | | | |
|---|---|---|---|---|
| Example | X | Y | Time (seconds) | Yellowing |
| L | 1.40 | 1.96 | 280 | 9 |
| M | 1.20 | 1.68 | 310 | 8 |
| N | 1.00 | 1.40 | 340 | 7 |
| O | 0.80 | 1.12 | 370 | 6 |
| P | 0.60 | 0.84 | 410 | 5 |
| Q | 0.40 | 0.56 | 560 | 4 |

In addition, compositions were prepared which included the hydroxyl-containing compound hydroxyethyl methacrylate, together with varying amounts of tertiary amine in the liquid binder and organic peroxide in the polymeric filler.

| Liquid Binder | Amount |
|---|---|
| Ethyl methacrylate | (84.00 − X)% |
| Hydroxyethyl methacrylate | 10.00 |
| Ethylene glycol dimethacrylate | 6.00 |
| N,N-dimethyl-p-toluidine | X |
| Total | 100.00 |

| POLYMERIC FILLER | |
|---|---|
| Poly(ethyl-co-methyl methacrylate) (70:30 mole ratio) | (100.00 − Y)% |
| Benzoyl peroxide | Y |
| Total | 100.00 |

| POLYMERIZATION | | | | |
|---|---|---|---|---|
| Example | X | Y | Time (seconds) | Yellowing |
| Q | 1.00 | 1.40 | 200 | 7 |
| R | 0.80 | 1.12 | 210 | 6 |
| S | 0.60 | 0.84 | 270 | 5 |
| T | 0.40 | 0.56 | 500 | 3 |

A comparison of Examples P and S above, which utilize the same levels of benzoyl peroxide and N,N-dimethyl-p-toluidine, effectively demonstrates the accelerating properties of the hydroxyl-containing compound, hydroxyethyl methacrylate. Thus, faster polymerization times are obtainable by the present inventive compositions at given levels of organic peroxide and tertiary amine, and, conversely, less yellowing is observed at equivalent polymerization times, as evidenced by a comparison of Examples S and L.

The following example represents a preferred embodiment of the present invention.

| Liquid Binder | Amount |
| --- | --- |
| Ethyl methacrylate | 82.20% |
| Hydroxyethyl methacrylate | 10.00 |
| Ethylene glycol dimethacrylate | 6.00 |
| N,N-dimethyl-p-toluidine | 0.80 |
| Tinuvin P | 1.00 |
| Total | 100.00% |
| POLYMERIC FILLER | |
| Poly(ethyl-co-methyl methacrylate) (70:30 mole ratio) | 98.88% |
| Benzoyl peroxide | 1.12 |
| | 100.00% |

The composition above, when combined in a ratio of 1.00 parts liquid binder to 2.70 parts polymeric filler, has a polymerization time of 210 seconds and a yellowing index score of 2.

Also contemplated within the scope of the present invention are compositions similar to the examples outlined above, but intended for use as self-polymerizing dental polymers, such as those utilized for denture, crown and bridge work.

What is claimed is:

1. A non-yellowing artificial fingernail composition consisting essentially of:
   (i) a liquid binder, by total weight:
      (a) from about 10 percent to about 95 percent of ethyl methacrylate;
      (b) from about 1 percent to about 50 percent of an unsaturated or saturated alcohol compound selected from the group consisting of hydroxyethyl methacrylate, hydroxypropyl methacrylate, isopropyl alcohol, and combinations thereof, and;
      (c) from about 0.1 percent to about 5.0 percent of a tertiary amine polymerization accelerator, selected from the group consisting of N,N-dimethyl-p-toluidine, N,N-dihydroxyethyl-p-toluidine, N,N-dimethyl aniline; and
   (ii) a polymeric filler portion, by dry weight of filler:
      (a) from about 95 percent to about 99.9 percent of a finely divided polymer selected from the group consisting of, poly(ethyl methacrylate), poly(methyl methacrylate), poly(ethyl-co-methyl methacrylate) and mixtures thereof,
      (b) from about 0.1 percent to about 5.0 percent of benzoyl peroxide,
      wherein said ratio of said binder and said filler portion are of a ratio of about one to three and give a composition that polymerizes in about 120 seconds to 360 seconds at ambient temperatures.

2. The artificial fingernail composition of claim 1 further consisting of from about 1 percent to about 80 percent of a di-, tri-, or multi-functional methacrylate crosslinker selected from the group consisting of ethylene glycol dimethacrylate, diethylene glycol dimethacrylate, triethylene glycol dimethacrylate, tetraethylene glycol dimethacrylate, poly(ethylene glycol) dimethacrylate, 1,3-butanediol dimethacrylate, 1,4-butanediol dimethacrylate, hexanediol dimethacrylate, 1,12-dodecanediol dimethacrylate, neopentyl glycol dimethacrylate, trimethylolpropane trimethacrylate, and combinations thereof.

3. The artificial fingernail composition of claim 1 wherein said liquid binder further consists of butylated hydroxytoluene (BHT) or methyl ether of hydroquinone (MEHQ).

4. The artificial fingernail composition of claim 1 wherein said liquid binder further consists of ultraviolet light stabilizers.

5. The artificial fingernail composition of claim 1 wherein said liquid binder further consists of dye.

6. The artificial fingernail composition of claim 1 wherein said polymeric filler portion further consists of additives selected from pigments, secondary polymers, and flow modifiers.

7. A non-yellowing artificial fingernail composition consisting essentially of:
   (i) a liquid binder, by total weight:
      (a) from about 10 percent to about 95 percent of a methacrylate monomer selected from the group consisting of ethyl methacrylate, n-butyl methacrylate, isobutyl methacrylate, n-propyl methacrylate, isopropyl methacrylate, tert-butyl methacrylate, and combinations thereof,
      (b) from about 1 percent to abut 50 percent of an unsaturated or saturated alcohol compound selected from the group consisting of hydroxyethyl methacrylate, hydroxypropyl methacrylate, hydroxybutyl methacrylate, propylene glycol monomethyl ether, diethylene glycol monomethyl ether, isopropyl alcohol, propylene glycol, 1,4-butylene glycol, neopentyl glycol monomethacrylate, and combinations thereof, and
      (c) from about 0.1 percent to about 5.0 percent of a tertiary amine polymerization accelerator, selected from the group consisting of N,N-dimethyl-p-toluidine, N,N-dihydroxyethyl-p-touidine, N,N-dimethyl aniline, and 4-(dimethylamino)phenethyl alcohol; and
      (d) from about 1 percent to about 80 percent of a di-, tri-, or multi-functional methacrylate crosslinker selected from the group consisting of ethylene glycol dimethacrylate, diethylene glycol dimethacrylate, triethylene glycol dimethacrylate, tetraethylene glycol dimethacrylate, poly(ethylene glycol) dimethacrylate, 1,3-butanediol dimethacrylate, 1,4-butanediol dimethacrylate, 1,6-hexanediol dimethacrylate, 1,12-dodecanediol dimethacrylate, neopentyl glycol dimethacrylate, trimethylolpropane trimethacrylate, and combinations thereof; and
      (e) a polymerization inhibitor of butylated hydroxytoluene (BHT) or methyl ether of hydroquinone (MEHQ); and
      (f) ultraviolet light stabilizers; and
   (ii) a polymeric filler portion, by dry weight of filler:

(a) from about 95 percent to about 99.9 percent of a finely divided polymer selected from the group consisting of, poly(ethyl methacrylate), poly(methyl methacrylate), poly(ethyl-co-methyl methacrylate), poly(butyl methacrylate), poly(methyl-co-butyl methacrylate), poly(vinyl acetate), poly(vinyl butyral) and poly(ethyl-co-butyl methacrylate) and mixtures thereof, (b) from about 0.1 percent to about 5.0 percent of an organic peroxide polymerization initiator, wherein said ratio of said binder and said filler portion are of a ratio of about one to three and give a composition that polymerizes in about 120 seconds to 360 seconds at ambient temperatures.

* * * * *

UNITED STATES PATENT AND TRADEMARK OFFICE
CERTIFICATE OF CORRECTION

PATENT NO. : 5,603,924
DATED : February 18, 1997
INVENTOR(S) : Montgomery

It is certified that error appears in the above-indentified patent and that said Letters Patent is hereby corrected as shown below:

In column 6 at line 14, please delete " for " and insert -- for 24 --.

In column 8, claim 2 at line 8, please delete " hexanediol " and insert -- 1,6-hexanediol --.

Signed and Sealed this

Fifth Day of August, 1997

Attest:

BRUCE LEHMAN

Attesting Officer

Commissioner of Patents and Trademarks